United States Patent
Sithambaram et al.

(10) Patent No.: US 7,355,075 B2
(45) Date of Patent: Apr. 8, 2008

(54) METHOD OF PRODUCING IMINES

(75) Inventors: Shanthakumar Sithambaram, Storrs, CT (US); Young-Chan Son, Storrs, CT (US); Steven L. Suib, Storrs, CT (US)

(73) Assignee: The University of Connecticut, Farmington, CT (US)

( * ) Notice: Subject to any disclaimer, the term of this patent is extended or adjusted under 35 U.S.C. 154(b) by 0 days.

(21) Appl. No.: 11/424,688

(22) Filed: Jun. 16, 2006

(65) Prior Publication Data

US 2007/0027344 A1 Feb. 1, 2007

Related U.S. Application Data

(60) Provisional application No. 60/691,210, filed on Jun. 16, 2005.

(51) Int. Cl.
*C07C 251/04* (2006.01)
*C07C 251/16* (2006.01)

(52) U.S. Cl. .................. 564/271; 564/272; 564/274; 564/278

(58) Field of Classification Search ............ 564/271, 564/272, 274, 278
See application file for complete search history.

(56) References Cited

U.S. PATENT DOCUMENTS

| | | |
|---|---|---|
| 4,618,501 A | 10/1986 | Parliment |
| 4,695,631 A | 9/1987 | Otsuka et al. |
| 5,103,058 A | 4/1992 | Pruett et al. |
| 6,476,268 B1 | 11/2002 | Winsel et al. |
| 6,770,595 B2 | 8/2004 | Plant et al. |

OTHER PUBLICATIONS

J.P. Adams, Imines, enamines and oximes, J.Chem. Soc., Perkin Trans. 1, 2000, 125-139.
Blackburn, et al., In Situ Oxidation-Imine Formation-Reduction Routes from Alcohols to Amines, Organic Letters, 2001, 1637-1639, vol. 3, No. 11.
R. Bloch, Addition of Organometallic Reagents to C=N Bonds: Reactivity and Selectivity, Chem. Rev., 1998, 1407-1438.
Brock, et al., A Review of Porous Manganese Oxide Materials, Chem. Mater., 1998, 2619-2628.
Cami-Kobeci, et al., Conversion of alcohols into N-alkyl via an indirect aza-Wittig reaction, Chem. Commun., 2004, 1072-1073.
Chakraborti, et al., Magnesium perchlorate as an efficient catalyst for the synthesis of imines and phenylhydrazones, Tetrahedron Letters 45, 2004, 7641-7644.
Crampton, et al., Some reactions of ammonia and primary amines with propanal, 2-chloroethanal, 2,2-dichloroethanal and 2,2,2-trichloroethanal in acetonitrile, J. Chem Soc., Perkin Trans. 2, 1997, 909-914.
Deguzman, et al., Synthesis and Characterization of Octahedral Molecular Sieves (OMS-2) Having the Hollandite Structure, Chem. Matter, 1994, 815-821.
Kanno, et al., A one-pot oxidation-immine formation-reduction route from alcohols to amines using manganese dioxide-sodium borohydride: the synthesis of naftifine, Tetrahedron Letters 43, 2002, 7337-7340.
Medvedeva, et al., Solvent-free MW-assisted direct conversion of 3-tri-organosilyl-(germyl)-prop-2-yn-1-ols to ynimines, ARKIVOC, 2003, 157-165.
S. Patai, The chemistry of the carbon-nitrogen double bond, 1971, 61-69 and 466-467, Interscience Publishers.
Shen, et al., Manganese Oxide Octahedral Molecular Sieves: Preparation, Characterization, and Applications, Science, 1993, 511-515, vol. 260.
Simion, et al., Synthesis of imines, diimines and macrocyclic diimines as possible ligands, in aqueous solution, J. Chem. Soc., Perkin Trans. 1, 2001, 2071-2078.
Son, et al., Efficient, Catalytic, Aerobic Oxidation of Alcohols with Octahedral Molecular Sieves, Angew. Chem. Int. Ed., 2001, 4280-4283, vol. 40, No. 22.
Takada, et al., Molecular Sieves in Ionic Liquids as an Efficient and Recyclable Medium for the Synthesis of Imines, Synlett, 2004, 2135-2138, No. 12.

*Primary Examiner*—Shailendra Kumar
(74) *Attorney, Agent, or Firm*—Cantor Colburn LLP

(57) ABSTRACT

A method for forming an imine comprises reacting a first reactant comprising a hydroxyl functionality, a carbonyl functionality, or both a hydroxyl functionality and a carbonyl functionality with a second reactant having an amine functionality in the presence of ordered porous manganese-based octahedral molecular sieves and an oxygen containing gas at a temperature and for a time sufficient for the imine to be produced.

15 Claims, No Drawings

METHOD OF PRODUCING IMINES

CROSS REFERENCE TO RELATED APPLICATIONS

This application claims priority to U.S. Provisional Patent Application No. 60/691,210 filed on Jun. 16, 2005, which is incorporated by reference in its entirety.

STATEMENT REGARDING FEDERALLY SPONSORED RESEARCH

The U.S. Government has certain rights in this invention pursuant to Department of Energy Grant No. DE-FG02-86ER13662.A0000.

BACKGROUND

Disclosed herein is a novel catalytic process for preparing imines by reacting amines with alcohols, carbonyls or combinations of alcohols and carbonyls.

Imines are highly useful in analytical materials, medicinal materials, polymer materials, liquid crystalline materials, and as synthons in organic synthesis. The production of imines from aldehydes, ketones or alcohols by reacting them with an aminating agent in the presence of a dehydrogenation catalyst is known. However, this approach can be expensive, inefficient, require harsh reaction conditions, and unsuccessful in the production of high molecular weight and/or branched imines. Additionally, many of the currently available methods have a negative environmental impact.

Accordingly, there is an ongoing need for efficient and environmentally friendly synthetic methods for the formation of imines.

SUMMARY

Disclosed herein is a method for forming an imine comprising:

reacting a first reactant comprising a hydroxyl functionality, a carbonyl functionality, or both a hydroxyl functionality and a carbonyl functionality with a second reactant having an amine functionality in the presence of ordered porous manganese-based octahedral molecular sieves and an oxygen containing gas at a temperature and for a time sufficient for the imine to be produced.

DETAILED DESCRIPTION

Disclosed herein is a method for making imines comprising reacting a first reactant having a hydroxyl functionality, a carbonyl functionality or a hydroxyl functionality and a carbonyl functionality with a second reactant having an amine functionality in the presence of ordered porous octahedral manganese-based molecular sieves and an oxygen containing gas. The reaction proceeds under relatively mild conditions. When the first reactant comprises a hydroxyl functionality the reactions proceeds as a "one pot" conversion without the need for isolation of the carbonyl containing intermediate. This is particularly valuable when the carbonyl containing intermediate is unstable or would be difficult to isolate. In addition, the method demonstrates high conversion rates and high selectivity.

As used herein, the terms "first," "second," and the like do not denote any order or importance, but rather are used to distinguish one element from another, and the terms "the", "a" and "an" do not denote a limitation of quantity, but rather denote the presence of at least one of the referenced item. Furthermore, all ranges reciting the same quantity or physical property are inclusive of the recited endpoints and independently combinable. The modifier "about" used in connection with a quantity is inclusive of the stated value and has the meaning dictated by the context or includes the degree of error associated with measurement of the particular quantity.

Ordered porous manganese-based octahedral molecular sieves (OMS) constitute an exemplary class of molecular sieves. These materials have one-dimensional tunnel structures and unlike zeolites, which have tetrahedrally coordinated species serving as the basic structural unit, these materials are based on six-coordinate manganese surrounded by an octahedral array of anions (e.g., oxide). The OMS framework architecture is dictated by the type of aggregation (e.g., corner-sharing, edge-sharing, or face-sharing) of the $MnO_6$ octahedra. The ability of manganese to adopt multiple oxidation states and of the $MnO_6$ octahedra to aggregate in different arrangements affords the formation of a large variety of OMS structures. The OMS may further comprise an additional transition metal within the molecular framework as long as the incorporation of the additional transition metal does not collapse the one dimensional tunnel structure.

In one embodiment, the OMS catalyst comprises todorokites. Todorokites include materials wherein the $MnO_6$ octahedra share edges to form triple chains and the triple chains share corners with adjacent triple chains to form a 3×3 tunnel structure. The size of an average dimension of these tunnels is about 6.9 Angstroms (Å). A counter cation, for maintaining overall charge neutrality, such as Na, Ca, Mg, and the like is present in the tunnels and is coordinated to the oxides of the triple chains. Todorokites are generally represented by the formula $(M)Mn_3O_7$, wherein M represents the counter cation and manganese is present in at least one oxidation state. Further, the formula may also include waters of hydration and is generally represented by $(M)_yMn_3O_7 \cdot xH_2O$, where y is about 0.3 to about 0.5 and x is about 3 to about 4.5.

In one embodiment, the OMS catalyst comprises hollandites. Hollandites include a family of materials wherein the $MnO_6$ octahedra share edges to form double chains and the double chains share corners with adjacent double chains to form a 2×2 tunnel structure. The size of an average dimension of these tunnels is about 4.6 Å. A counter cation for maintaining overall charge neutrality such as Ba, K, Na, Pb, and the like, is present in the tunnels and is coordinated to the oxides of the double chains. The identity of the counter cation determines the mineral species or structure type. Hollandites are generally represented by the formula $(M)Mn_8O_{16}$, wherein M represents the counter cation and manganese is present in at least one oxidation state. Further, the formula may also include waters of hydration and is generally represented by $(M)_yMn_8O_{16} \cdot xH_2O$, where y is about 0.8 to about 1.5 and x is about 3 to about 10. Suitable hollandites include hollandite ($BaMn_8O_{16}$), cryptomelane ($KMn_8O_{16}$), manjiroite ($NaMn_8O_{16}$), coronadite ($PbMn_8O_{16}$), and the like, and variants of at least one of the foregoing hollandites. In one embodiment, the OMS catalyst comprises cryptomelane-type materials. In some embodiments some or all of the counter cation is $H^+$.

In one embodiment, the OMS catalyst has an average Mn oxidation state of about 3 to about 4. Within this range the average oxidation state may be greater than or equal to about 3.2, or, more specifically, greater than or equal to 3.2, or even more specifically, greater than or equal to about 3.3. Average oxidation state may be determined by potentiometric titration.

In an exemplary method the OMS catalyst can be prepared by combining an aqueous solution of $KMnO_4$ (0.2 to 0.6 molar), an aqueous solution of $MnSO_4.H_2O$ (1.0 to 2.5 molar) and a concentrate acid such as $HNO_3$. The aqueous solution is refluxed at 100° C. for 18-36 hours. The product is filtered, washed and dried, typically at a temperature of 100 to 140° C. Similar procedures are known in the literature, for example, DeGuzman et al., Chem. Mater. 1994, 6, 815-821.

The OMS may be used in any form that is convenient, such as particulate, aggregate, film or combination thereof. In addition, the OMS may be affixed to a substrate to facilitate separation of the catalyst from the product.

In addition, the OMS catalyst can be reused. If desired, the catalyst can be regenerated by washing with methanol, water or a combination of water and methanol and subjecting the washed catalyst to a temperature of about 150° C. to about 300° C. for about 6 to 24 hours in the presence of oxygen. Temperatures greater than about 310° C. may be undesirable because they may result in a phase change in the catalyst.

The molar ratio of OMS catalyst to the first reactant can be about 0.0625 to about 0.5. However, the molar ratio is dependent upon molecular weight and the number of available active sites. Within this range the ratio of OMS catalyst to first reactant may be greater than or equal to 0.08, or, more specifically, greater than or equal to 0.10. Also within this range the ratio of OMS catalyst to first reactant may be less than or equal to 0.45, or, more specifically, less than or equal to 0.4.

The first reactant comprises a hydroxyl functionality, a carbonyl functionality or a hydroxyl functionality and a carbonyl functionality. The first reactant may be an aliphatic or aromatic compound provided that the first reactant is a liquid or solid at the reaction temperature.

The first reactant may comprise any number of carbons as long as the structure of the reactant does not prevent the formation of the imine. For example, when the first reactant comprises a hydroxyl functionality, the reaction proceeds through a carbonyl intermediate and the carbonyl intermediate must be sufficiently stable under the reaction conditions for the conversion of the carbonyl to the imine to occur. Similarly the hydroxyl functionality and/or carbonyl functionality must be sufficiently accessible to allow activation by the catalyst. A hydroxyl functionality and/or carbonyl functionality located in a sterically hindered space may be less likely to interact with the catalyst.

The hydroxyl functionality may be primary or secondary although, as appreciated by one of ordinary skill in the art, a primary hydroxyl functionality is typically more reactive and thus will have shorter reaction times than a comparable compound having a secondary hydroxyl functionality. Also a reactant having an aldehyde functionality is expected to be more reactive than a reactant having an ketone functionality.

In some embodiments the first reactant may comprise multiple hydroxyl functionalities, multiple carbonyl functionalities or combinations thereof In addition the first reactant may comprise additional functionalities. The additional functionalities may be electron donating or electron withdrawing as long as their presence does not prevent reaction with the amine to form the imine.

Exemplary first reactants include primary alcohols comprising a substituted or unsubstituted aromatic ring; straight or branched chain primary alcohols that may be saturated or unsaturated; diols comprising a saturated or unsaturated carbon chain that may be straight or branched, a substituted or unsubstituted aromatic ring or a combination thereof; a secondary alcohol comprising a cycloaliphatic ring; straight chain or branched chain aldehydes that may be substituted with other functional groups including monocyclic or polycyclic aromatic groups; straight chain or branched chain ketones that may be substituted with other functional groups including monocyclic or polycyclic aromatic groups; straight or branched chains comprising both a ketone and a hydroxyl functionality and optionally further comprising other functionalities; straight or branched chains comprising both an aldehyde and a hydroxyl functionality, optionally further comprising other functionalities; and the like.

The second reactant comprises an amine functionality. The second reactant may be an aliphatic or aromatic compound provided that the second reactant is a liquid or solid at the reaction temperature.

The amine functionality may be primary, secondary or tertiary although a primary amine is typically more reactive than a secondary amine and a secondary amine is typically more reactive than a tertiary amine. Similar to the preceding discussion with regard to the first reactant, there is no particular limitation on the number of carbon atoms present in the reactant as long as the structure of the reactant does not prevent the formation of the imine.

In one embodiment the first reactant comprises an alkyl alcohol and the second reactant comprises a secondary amine.

Exemplary second reactants include straight or branched chain primary amines optionally comprising additional functionalities such as an aromatic ring; straight or branched chain primary diamines optionally comprising additional functionalities such as an aromatic ring; straight chain, branched chain or cycloaliphatic secondary amines optionally comprising additional functionalities such as an aromatic ring; straight chain, branched chain or cycloaliphatic secondary diamines optionally comprising additional functionalities such as an aromatic ring; straight chain, branched chain or cycloaliphatic diamines comprising both a primary and a secondary amine optionally comprising additional functionalities such as an aromatic ring, and the like.

The reaction may be performed in the presence of a solvent. The solvent is typically chosen based on its ability to dissolve the reactants. Typically the reaction is performed at reflux when the first reactant comprises a hydroxyl functionality. In some embodiments the boiling point of the solvent is sufficient to attain a high enough reflux temperature for oxidation of the hydroxyl to the carbonyl. When the first reactant comprises a ketone functionality or an aldehyde functionality the reaction may be run at room temperature.

In one embodiment the first reactant comprises both a hydroxyl functionality and a carbonyl functionality and the temperature of the reaction is selected to selectively react the carbonyl functionality with the second reactant having an amine functionality.

The solvent may be protic, aprotic or a combination of protic and aprotic solvents. Exemplary solvents include toluene, octane, xylene, benzene, n-butanol, and acetonitrile.

In some embodiments the solvent is a non-polar, aprotic solvent such as toluene. Solvents comprising hydroxyl functionalities, carbonyl functionalities or amine functionalities may be used as long as the solvent does not participate in the reaction in place of the reactant.

In some embodiments, when one or both of the reactants is in liquid form at the reaction temperature a solvent may not be required.

Suitable oxygen containing gases include air, oxygen gas, and mixtures of oxygen gas with other gases such as nitrogen or argon. In some embodiments the oxygen containing gas is a flowing oxygen containing gas. In other embodiments the reaction vessel is charged with the oxygen containing gas. Subsequent additions of the oxygen containing gas may be made as necessary.

The reactants, optional solvent, and catalyst are typically combined in a reaction vessel and stirred to form a reaction mixture. The reaction mixture is typically maintained at the desired reaction temperature with stirring for a time sufficient to form the imine in the desired quantity. The progress of the reaction toward the imine may be followed using an appropriate method such as thin layer chromatography, nuclear magnetic resonance, high pressure liquid chromatography, gas chromatography or a combination of the foregoing methods. Exemplary reaction times are about 2 to about 60 hours. The catalyst is typically removed from the reaction mixture using any solid/liquid separation technique such as filtration, centrifugation, and the like or a combination of separation methods. The product may be isolated using standard isolation techniques.

The invention is further illustrated by the following non-limiting examples.

EXAMPLES

Catalyst Preparation

The preparation of the OMS catalyst used in the examples is as follows. 225 milliliters (ml) of potassium permanganate solution (0.4 Molar) was added to a mixture of 67.5 ml manganese sulfate hydrate solution (1.75 Molar) and 6.8 ml of concentrated nitric acid in a 500 ml of round bottom flask with a condenser. The dark brown slurry was refluxed for 24 hours, then filtered and washed with deionized water several times. The catalyst was dried at 120° C. overnight before use. The composition of the K-OMS-2 catalyst was $KMn_8O_{16} \cdot nH_2O$ and the tunnels had dimensions of 4.6×4.6 angstroms. The average oxidation state of the manganese was approximately 3.8. The H-K-OMS-2 catalyst was generated by stirring the K-OMS-2 catalyst in a 1 molar solution of nitric acid for 6 hours at 60-70° C. for 6 hours.

The above described catalysts were used to make imines from reactants having amines and reactants having hydroxyl functionality or both hydroxyl and carbonyl functionalities. One millimole of alcohol, 10 milliliters of toluene, 3 to 5 millimoles of amine and 50 milligrams of catalyst were added to a 50 milliliter flask. The mixture was stirred at reflux for 12 to 24 hours at 110° C. in air. After the reaction time the mixture was cooled and the catalyst was removed by filtration. The product mixture was analyzed by gas chromatography-mass spectrometry [GC-MS]. The reactants, products, catalyst, and time are shown in Table 1.

TABLE 1

| | Reactant 1 | Reactant 2 | Catalyst | Time |
|---|---|---|---|---|
| 1 | benzyl alcohol (PhCH₂OH) | H₂N-butyl | K—OMS-2 | 12 hours |
| 2 | 4-chlorobenzyl alcohol | H₂N-butyl | K—OMS-2 | 12 hours |
| 3 | 4-methylbenzyl alcohol | H₂N-butyl | K—OMS-2 | 24 hours |
| 4 | cinnamyl alcohol | H₂N-butyl | H—K—OMS-2 | 12 hours |
| 5 | cinnamyl alcohol | H₂N-butyl | K—OMS-2 | 12 hours |
| 6 | 3-methyl-1-butanol | H₂N-butyl | K—OMS-2 | 12 hours |

TABLE 1-continued

| # | Alcohol | Amine | Catalyst | Time |
|---|---------|-------|----------|------|
| 7 | cyclopentanol | H₂N-propyl (n-butylamine) | K—OMS-2 | 12 hours |
| 8 | cyclohexanol | n-butylamine | K—OMS-2 | 12 hours |
| 9 | 1-phenylethanol | n-butylamine | K—OMS-2 | 24 hours |
| 10 | 1,2-benzenedimethanol | n-butylamine | K—OMS-2 | 24 hours |
| 11 | 1,3-benzenedimethanol | n-butylamine | K—OMS-2 | 24 hours |
| 12 | 1,4-benzenedimethanol | n-butylamine | K—OMS-2 | 24 hours |
| 13 | benzoin | n-butylamine | K—OMS-2 | 24 hours |
| 14 | 1,4-benzenedimethanol | aniline | K—OMS-2 | 48 hours |
| 15 | benzyl alcohol | aniline | K—OMS-2 | 24 hours |
| 16 | 4-methoxybenzyl alcohol | aniline | K—OMS-2 | 24 hours |
| 17 | 4-methylbenzyl alcohol | aniline | K—OMS-2 | 24 hours |

TABLE 1-continued

| | Alcohol | Amine | Catalyst | Time |
|---|---|---|---|---|
| 18 | 4-nitrobenzyl alcohol | aniline | K—OMS-2 | 24 hours |
| 19 | 4-chlorobenzyl alcohol | aniline | K—OMS-2 | 24 hours |
| 20 | 2-thiophenemethanol | n-butylamine | K—OMS-2 | 24 hours |
| 21 | 2-thiophenemethanol | aniline | K—OMS-2 | 24 hours |
| 22 | cinnamyl alcohol | aniline | K—OMS-2 | 24 hours |
| 23 | cinnamyl alcohol | aniline | H—K—OMS-2 | 24 hours |
| 24 | benzoin | ethylenediamine | K—OMS-2 | 24 hours |

| | Product | Conversion | Selectivity |
|---|---|---|---|
| 1 | N-benzylidene-n-butylamine | 100% | 99% |
| 2 | N-(4-chlorobenzylidene)-n-butylamine | 100% | 99% |
| 3 | N-(4-methylbenzylidene)-n-butylamine | 100% | 99% |
| 4 | N-cinnamylidene-n-butylamine | 99% | 99% |

TABLE 1-continued
| | | | |
|---|---|---|---|
| 5 | 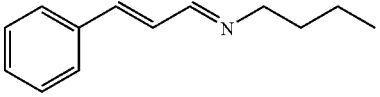 | 100% | 80% |
| 6 | 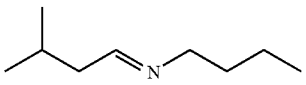 | 100% | 44% |
| 7 | 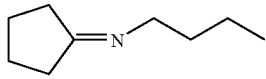 | 100% | 25% |
| 8 | 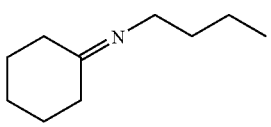 | 100% | 12% |
| 9 | 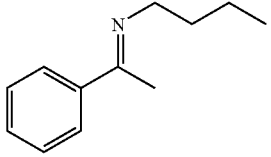 | 64% | 10% Imine<br>90% Ketone |
| 10 | 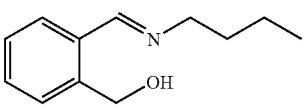 | 100% | 78% |
| 11 | 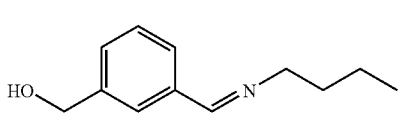 | 100% | 80% |
| | 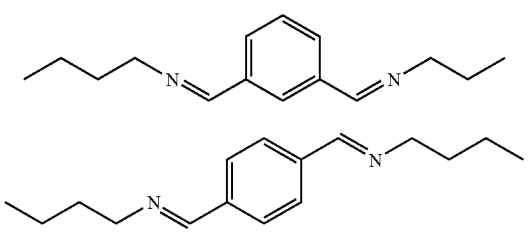 | 100% | 20% |
| 12 | | 100% | 100% |
| 13 | 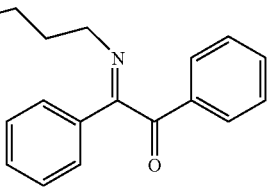 | 100% | 76% |
| | | 100% | 24% |
| 14 | 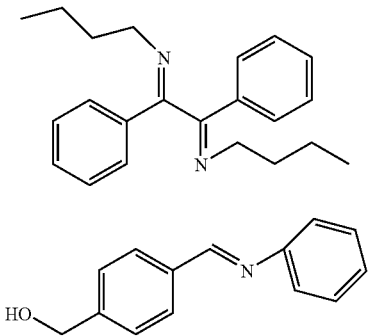 | 100% | 22% |

TABLE 1-continued
| | Structure | | |
|---|---|---|---|
| | 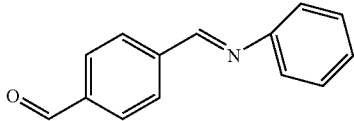 | 100% | 29% |
| | 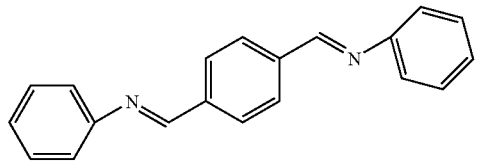 | 100% | 49% |
| 15 | 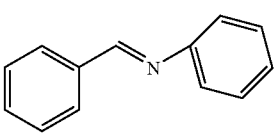 | 99% | 100% |
| 16 | 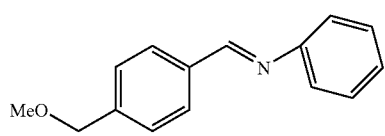 | 77% | 71% |
| 17 | 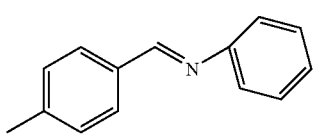 | 89% | 90% |
| 18 | 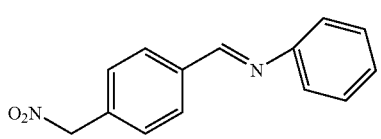 | 100% | 100% |
| 19 | 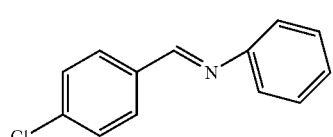 | 100% | 99% |
| 20 | 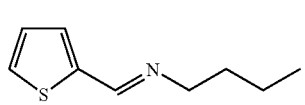 | 97% | 100% |
| 21 | 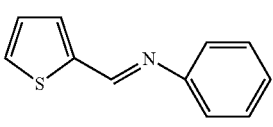 | 75% | 100% |
| 22 | 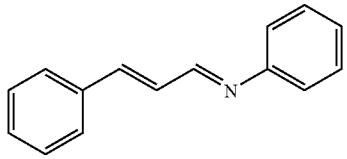 | 58% | 74% |
| 23 | 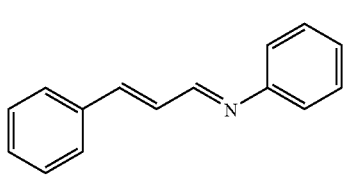 | 61% | 84% |

TABLE 1-continued

| 24 | 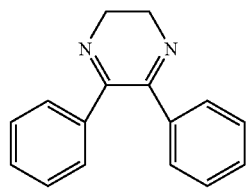 | 100% | 100% |

Please verify the data for the examples in red.

Examples 1 through 3 demonstrate that high selectivity and conversion can be achieved when reactant 1 is a primary benzylic alcohol. Examples 4 and 5 demonstrate the high selectivity and conversion that can be achieved using allylic alcohols. Additionally, Examples 4 and 5 show that the identity of the catalyst can affect the selectivity and conversion of the reaction. Examples 6 through 9 employ secondary alcohols. The secondary alcohols show lower conversions compared to primary alcohols, probably due to steric effects. Examples 10 through 12 employ a dihydroxy compounds as the hydroxy containing compound and show that among ortho, meta and para dihydroxy compounds, para dihydroxy compounds have the highest selectivity. Example 13 uses a compound having both a carbonyl and a hydroxy group as reactant 1 and the di-imine is produced.

Example 14 was checked at 24 and 48 hours and gives information regarding the likely reaction pathway of the imine synthesis. After 24 hours only the imine—hydroxy compound was present indicating a sequential pathway for di-imine formation.

Example 15 provides a basis for comparison of varying substituents on the aromatic ring. Examples 16-17 demonstrate the effects of substituents on the reaction. Example 16 shows that the presences of a strong electron donating group results in lower conversion and selectivity compared to the situation when no substituent is present. A weak electron donating group, such as found in Example 16, shows a conversion and selectivity between that of a strong electron donating group and no substituent. Electron withdrawing groups, as demonstrated by Examples 18 and 19, show little or no decrease in conversion or selectivity.

Examples 20 and 21 show the relative steric effects of the nucleophiles. Butyl amine gave a significantly higher conversion than aniline. Examples 22 and 23 further explore the effects of different catalysts on selectivity and conversion, similar to Examples 4 and 5.

As can be seen from the foregoing examples the OMS catalyst can be used to facilitate the reaction between a wide variety of first reactants (having hydroxyl functionality, ketone functionality, aldehyde functionality or a combination of the foregoing functionalities) with a wide variety of second reactants having an amine functionality. These reactions proceeded under mild conditions and showed selectivities and conversions of up to 100%.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for forming an imine comprising:
   reacting a first reactant comprising a hydroxyl functionality, a carbonyl functionality, or both a hydroxyl functionality and a carbonyl functionality with a second reactant having an amine functionality in the presence of ordered porous manganese-based octahedral molecular sieves and an oxygen containing gas at a temperature and for a time sufficient for the imine to be produced, wherein the ordered porous manganese-based octahedral molecular sieves are present in a catalytic amount.

2. The method of claim 1 wherein the ordered porous manganese-based octahedral molecular sieves comprise todorkites.

3. The method of claim 1 wherein the ordered porous manganese-based octahedral molecular sieves comprise hollandites.

4. The method of claim 1 wherein the ordered porous manganese-based octahedral molecular sieves have an average manganese oxidation state of about 3 to about 4.

5. The method of claim 1 wherein the hydroxyl functionality is a primary hydroxyl functionality.

6. The method of claim 1 wherein the molar ratio of ordered porous manganese-based octahedral molecular sieves to the first reactant is about 0.0625 to about 0.5.

7. The method of claim 1 wherein the amine functionality is a primary amine functionality.

8. The method of claim 1 wherein the first reactant, the second reactant or both the first reactant and the second reactant are dissolved in a solvent.

9. The method of claim 8 wherein the solvent is a non-polar aprotic solvent.

10. The method of claim 1 wherein the first reactant comprises a hydroxyl functionality and a carbonyl functionality and the temperature of the method is chosen to selectively react the carbonyl functionality with the second reactant.

11. The method of claim 1 wherein the oxygen containing gas is air.

12. The method of claim 1 wherein the ordered porous manganese-based octahedral molecular sieves have been recycled.

13. The method of claim 1 wherein the oxygen containing gas is flowing.

14. The method of claim 1 wherein the ordered porous manganese-based octahedral molecular sieves further comprise an additional transition metal.

15. A method for forming an imine comprising:
reacting a first reactant comprising a primary hydroxyl functionality, a carbonyl functionality, or both a primary hydroxyl functionality and a carbonyl functionality with a second reactant having a primary amine functionality in the presence of ordered porous manganese-based octahedral molecular sieves and an oxygen containing gas at a temperature and for a time sufficient for the imine to be produced, wherein the ordered porous manganese-based octahedral molecular sieves are present in a catalytic amount.

* * * * *